United States Patent [19]

Atalar et al.

[11] Patent Number: 5,115,414
[45] Date of Patent: May 19, 1992

[54] CONICAL ULTRASONIC WAVE DEFLECTION SYSTEM

[76] Inventors: Abdullah Atalar, Bilkent Univ. Loj. 8/4, P.K. 8, Maltepe/Ankara 06572; Hayrettin Koeymen, Guniz Sok. No: 34/10,, Kavaklidere/Ankara, both of Turkey

[21] Appl. No.: 581,721

[22] Filed: Sep. 12, 1990

[30] Foreign Application Priority Data

Sep. 16, 1989 [DE] Fed. Rep. of Germany ....... 3931048

[51] Int. Cl.$^5$ .............................................. G03B 42/06
[52] U.S. Cl. ........................................ 367/7; 367/138; 367/150; 367/151; 73/642
[58] Field of Search ............... 367/7, 150, 151, 138; 73/644, 642, 629; 128/663.01; 181/176

[56] References Cited

U.S. PATENT DOCUMENTS

| | | | |
|---|---|---|---|
| 3,262,307 | 7/1966 | Hart | 73/642 |
| 4,576,048 | 3/1986 | Glenn | 73/642 |
| 4,779,241 | 10/1988 | Atalar et al. | 367/104 |

OTHER PUBLICATIONS

Zieniuk et al., "Ultrasonic Pin Scanning Microscope A New Approach to Ultrasonic Microscopy", 1986 Ultrasonics Symposium, IEEE, 1986, pp. 1037-1039.
Smith et al., "Confocal surface acoustic wave microscopy", Appl. Phys. Lett. 42(5), Mar. 1, 1983, pp. 411, 413.
Nongaillard et al., "A new focusing method for nondestructive evaluation by surface acoustic wave", J. Appl. Phys., 55(1), Jan. 1, 1984, pp. 75, 77, 79.
Ayter, "Focusing Surface Waves Using Conical Transducers", 1987 Ultrasonics Symposium, 1987 IEEE, pp. 301-304.
Atalar et al., "Measurement of Sensitivity of Different Wave Modes to Sub-surface Defects", 1988 Ultrasonics Symposium, 1988 IEEE, pp. 771-774.
Atalar et al., "A High Efficieny Lamb Wave Lens for Subsurface Imaging", Proc. IEEE, Ultrason, Symp., 1989, Oct. 3, 1989.
Krautkrämer et al., "Werkstoffprüfung mit Ultraschall", Springer-Verlag, 1986, pp. 34-38, 608-611 (no translation).

*Primary Examiner*—Daniel T. Pihulic
*Attorney, Agent, or Firm*—Foley & Lardner

[57] ABSTRACT

A conical ultrasonic wave deflection system has an ultrasonic transducer for ultrasonic microscopy using surface waves and/or Lamb waves in an object. A conical wave front is directed onto the object via a deflection element. An inactive axial circular disk is provided between the ultrasonic transducer and the object to minimize unnecessary interference from undeflected waves. A frustoconical lens with a blocked top face, or a conical metal reflector with a ring transducer on the transducer side can be provided as the deflection element. The arrangement is highly compatible with ultrasonic microscopes. Matching to a critical angle $\theta$ of the object is achieved by selection of the appropriate ultrasonic frequency.

29 Claims, 2 Drawing Sheets

CONICAL ULTRASONIC WAVE DEFLECTION SYSTEM

BACKGROUND OF THE INVENTION

The invention relates to a conical ultrasonic wave deflection system having an axially symmetric ultrasonic transducer for ultrasonic microscopy utilizing surface waves and/or Lamb waves in an object.

An ultrasonic point scanning microscope is discussed in J. K. Zieniuk, A. Latuszek, Proc. IEEE Ultrason. Symp. (1986), pp. 1037-1039. In this microscope, a frustoconical sapphire point is mounted on an ultrasonic transducer. The point diameter is approximately ¼ of the ultrasonic wavelength in the coupling medium. Defined waves are thus not formed in the coupling medium and the arrangement results in overresolution.

A cone angle of 20°, a point diameter of 20 μm and an ultrasonic frequency of 30 MHz are discussed in this article for excitation of longitudinal waves in the object. The conical shape serves primarily for making the transition from the large ultrasonic transducer face to a small point.

An arrangement for ultrasonic microscopy utilizing surface waves and spherical ultrasonic lenses is discussed by I. R. Smith et al. in Appl. Phys. Lett. (42), 1983, pp. 411-413.

In the Smith et al. device, in the defocused state, the signal components of the longitudinal waves are suppressed, while ultrasonic waves passing through a narrow ring on the spherical lens impinge on the surface of the object at a suitable angle, the Rayleigh angle, for resonant excitation of surface waves, and generate surface waves, with a circular wave front, which converge to a diffraction-limited surface wave focus. A transmission arrangement including a transmitting and receiving unit having a lens and an ultrasonic transducer is also disclosed.

For a reflecting arrangement, only a semicircular sector of a conventional spherical lens/transducer unit is proposed. Either the lens is divided or a semicircular ultrasonic transducer is provided.

In the Smith et al. device, it is not possible to specify a particular angle of incidence on the surface and thus select, for example, particular modes of surface waves. The fact that in the Smith et al. device only a very small part of the ultrasonic energy which is generated and acts on the object is converted into surface waves, and thus used for signal generation, has led to development of a number of other devices.

An arrangement which is intended to avoid the disadvantages of the Smith et al. device is discussed by B. Nongaillard et al. in J. Appl. Phys. 55 (1984), pp. 75-79. In this device, a cylindrical lens is provided instead of a spherical lens, and the longitudinal axis of the cylindrical lens is inclined with respect to the surface of the object. Cylindrical wave fronts then have an elliptical line of intersection with the surface of the object. If the angle of inclination corresponds to the Rayleigh angle, then surface waves are generated which, however, due to the elliptical generation zone, converge to a line focus on the surface. The required inclination of the cylindrical lens with respect to a perpendicular to the surface of the object is impractical for application to a conventional ultrasonic microscope.

In U.S. Pat. No. 4,779,241, issued to Atalar et al., a plane ultrasonic transducer acts at an oblique angle on a reflecting or diffracting, preferably parabolically cylindrical, face so that conical wave fronts are produced, the cone axis coinciding with the focus line of the reflecting or diffracting face. The objective is arranged perpendicular to this axis, and the intersecting line of the conical wave fronts with the surface of the object is then a circular sector, so that a point focus similar to the Smith et al. device is obtained. By varying the angle between the ultrasonic transducer and the focusing face, the Rayleigh angle for generating surface waves is obtained.

This technique can be carried out for transmission and reflection, with separate or unified transmitting and receiving ultrasonic transducers. However, due to the oblique angle required, it is difficult to make this method compatible with a conventional ultrasonic microscope.

It has also been proposed to utilize the shape of the ultrasonic transducer to achieve a desired wave geometry. An ultrasonic transducer in the form of a cone sector, the cone axis of which is perpendicular to the surface of the object, is discussed by S. Ayter in Proc. of 1987 IEEE Ultrason. Symp., pp. 301-304.

This technique, however, requires a significantly increased manufacturing outlay for making the ultrasonic transducer.

It is known from A. Atalar et al., Proc. 1988 IEEE Ultrason. Symp., pp. 771-774 that the excitation of generalized Lamb waves can be used advantageously for ultrasonic image generation on objects with a layer structure.

SUMMARY OF THE INVENTION

An object of the invention is to provide an ultrasonic wave deflection system of wide applicability which generates surface waves with a circular wave front in the object, having at the same time as simple a construction as possible, high image quality and good compatibility with ultrasonic microscopes.

It is a further object of the invention to provide techniques for effective ultrasonic microscopy with such an arrangement.

It is another object of the invention to provide an ultrasonic wave deflection system which effectively suppresses interference from undesirable excitation and irradiation mechanisms.

The invention provides a conical ultrasonic wave deflection system which includes an ultrasonic transducer generating ultrasonic waves for ultrasonic microscopy using at least one of surface waves or Lamb waves in an object under examination. The system also includes an ultrasonic deflection element deflecting ultrasonic waves generated by the ultrasonic transducer to direct a conical wave front onto the object. The conical wavefront is defined by the deflection cone axis. The ultrasonic transducer and the ultrasonic deflection element prevent a portion of the object in the vicinity of the deflection cone axis from being influenced by undeflected waves.

In a preferred embodiment, the ultrasonic transducer includes a hole axially aligned with the deflection cone axis to prevent a portion of the object in the vicinity of the deflection cone axis from being influenced by undeflected waves.

The ultrasonic deflection element can include an inactive disk axially aligned with the deflection cone axis to prevent a portion of the object in the vicinity of the deflection cone axis from being influenced by undeflected waves.

Further objects, features, and advantages of the invention will become apparent from the following detailed description.

BRIEF DESCRIPTION OF THE DRAWINGS

The invention will be described in greater detail below with reference to the drawings, wherein.

DETAILED DESCRIPTION OF THE PREFERRED EMBODIMENTS

Figure 1:
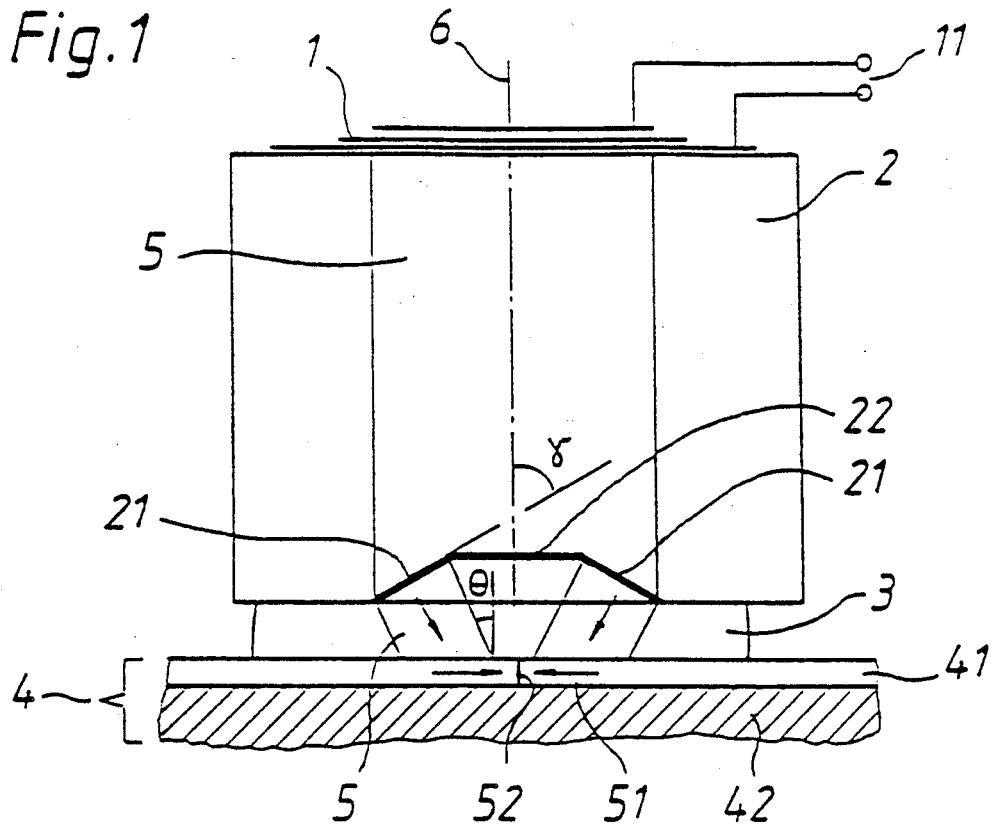
FIG. 1 shows a sectional view of a preferred embodiment with a conical lens.

The conditions required for effective generation of a surface wave focus are:

(1) All ranges of ultrasonic waves have the same particular angle, namely a critical angle corresponding to the Rayleigh wave or a mode of a Lamb wave, with respect to the surface of the object.

(2) The wave fronts impinge on a circle or a circular sector on the surface.

In the invention, a conical wave front of exciting ultrasonic waves is generated by an arrangement including a plane or a conical ultrasonic transducer and a conical deflection element with a common axis of symmetry, with the surface of the object perpendicular to the cone axis.

The covering or cutting-out of an axially symmetric circle on the ultrasonic transducer and/or on the deflection element effectively suppresses interference from other excitation and irradiation mechanisms. Moreover, chamfering and roughening on the outside of the conical surface of the lens will prevent spurious signals.

No oblique-angled component arrangements are required in the invention. The focus lies as a line on the cone axis perpendicular to the surface of the object, thus forming a point on the surface, whereas in conventional arrangements, with cylindrical faces, it is oblique. This improves image quality.

In particular, one embodiment with a diffracting deflection element, that is, an ultrasonic lens, is directly compatible with customary ultrasonic microscopes, where the embodiment can be employed instead of a transducer/spherical lens unit. It is largely insignificant from a manufacturing perspective if a conically concave face is used in place of a spherically concave face, such as in the I. R. Smith et al. device discussed above.

It would initially appear to be a problem of the proposed arrangement that the angle of incidence of the ultrasonic waves on the surface of the object is defined by the generating angle of the cone, and that this angle does not correspond to a critical angle for the generation of surface waves or Lamb waves in a particular object. The proposed technique solves this problem by means of frequency tuning.

In particular, waves known as "Lamb waves" are dispersive in surface layers, so the conical deflection element can be matched to the prescribed angle by suitably selecting the frequency corresponding to the critical angle for a "Lamb wave".

Experimentation to determine this frequency is simple and consists of varying the frequency until the maximum signal is received. Since the bandwidth of most ultrasonic transducers is not great, however, a range of proposed arrangements with different cone angles is required to be able to examine all possible objects.

An ultrasonic microscope having such an arrangement has an axial resolution equal to the thickness of the surface layer in which the excited Lamb wave modes run. On the other hand, it is not easy to define the lateral resolution. The received signal is always disturbed whenever a structure lies somewhere within the range of the surface wave converging in a circular way, although the interference is greatest when the structure lies at the focus. Particularly for small structures, however, lateral resolutions better than the ultrasonic wavelength can be obtained.

An exemplary embodiment of the invention with a diffracting deflection face is illustrated in FIG. 1.

In FIG. 1, a piezoelectric ultrasonic transducer 1 is provided with terminals 11 for electrical high-frequency excitation and is mounted on a lens body 2, made of sapphire, for example. A coupling medium 3, for example water, provides the connection to an object 4 through which ultrasonic waves 5 are transmitted. In contrast to conventional spherical lenses, the diffracting face 21 is designed as a cone with a cone angle $\gamma$, to be precise, a truncated cone with a plane passive and inactive top face 22, which is covered with a highly ultrasonic damping layer, in order to prevent ultrasonic waves from impinging perpendicularly to the object. The diffracting face 21 has an anti-reflection coating. The chamfered and roughened surface 24 prevents spurious signals.

The object 4 to be examined should preferably have a surface layer 41 on a substrate 42, which itself may in turn consist of layers. For example, a copper foil bonded to aluminum may be examined.

After diffraction at the face 21, ultrasonic waves 5, which all have the same angle $\theta$ with respect to the cone axis 6, the common wave front of which is conical, run in the coupling medium 3.

The angle $\theta$ is obtained from the cone angle $\gamma$ in accordance with Snellius' law of diffraction as a function of the speed of sound in the lens body 2 and the coupling medium 3.

The cone axis 6 is aligned to be perpendicular to the surface of the object 4 so that the wave fronts intersect the surface of the object in a circular fashion.

If the angle $\theta$ corresponds to the critical angle for particular surface waves or Lamb waves 51, then these waves are greatly excited. The circular geometry of the intersection of the wave fronts with the surface causes a radial propagation of the surface or Lamb waves 51 to a focus 52. Lamb waves which only propagate in surface layer 41 are preferably excited. These waves are dispersive. The critical angle corresponds to the angle $\theta$ prescribed by the lens 2 for a Rayleigh or a Lamb wave mode within wide limits by varying the ultrasonic frequency.

Due to the existence of coupling medium 3, Lamb waves are leaky, that is, they radiate back greatly into the coupling medium 3 and thus lead to a detectable ultrasonic signal.

The described arrangement can serve in a reflection ultrasonic microscope as a transmitter and a receiver simultaneously, in which case it is necessary to provide conventional circuitry for decoupling excitation and measurement signals. Time separation of the transmitting and the measuring wave can be achieved by use of the time required for waves to traverse the length of the lens body 2, and the path in coupling medium 3 and surface layer 41.

The distance between the object 4 and the lens 2 must be chosen small enough so that the specular reflections of the conical wave from the object surface are avoided.

It is also possible to use the embodiment as a transmitter in a transmission ultrasonic microscope, in which case a similar or another known arrangement is provided as a receiver on the opposite object side.

It is known from Smith et al., discussed above, that a reflecting arrangement with full circular symmetry about an axis 6 delivers a maximum signal in the case of a structureless surface, and does this even if an ideal reflector is situated exactly at the focus 52. If the structure is located a little to the side of the focus 52, image information is obtained using the signal drop.

A refinement is obtained if the arrangement is effectively halved to form a 180° sector. Besides dividing the entire arrangement into a symmetrical plane containing the axis 6, one half of the diffracting face 21 is covered with absorber material and/or the ultrasonic transducer is limited to a 180° sector. Deviations from the 180° sector angle lead to proportional impairments of the useful effects. A null measurement is then obtained which delivers no signal without a point of interference in the focus 52 and a maximum signal with a point of interference in the focus 52.

An ultrasonic lens 2 with a conical diffraction face 21 can be completely manufactured using known production technology for spherical ultrasonic lenses, and can be used in place of spherical ultrasonic lenses in ultrasonic microscopes. It is possible to manufacture conical arrangements with cone diameters down to 10 $\mu$m in order to obtain high resolution.

As a general rule, the smallest diameter of the cone is selected to be more than several ultrasonic wavelengths in the coupling medium at the frequency used.

If the angle $\theta$ is small, then the path length of the ultrasonic waves 5 in the coupling medium 3 are substantially shorter than the path length with comparable spherical lenses, which increases the range of utilizable ultrasonic frequencies in the GHz range, and hence better resolution is achieved.

Advantageous ultrasonic frequencies for this ultrasonic wave deflection system lie in the range from 1 MHz to 10 GHz.

Since the focus onto the surface layer 41 remains restricted in the axial direction, and cannot drift laterally out as a result of the orthogonal arrangement, when the distance between lens 2 and object 4 changes, for example when the microscope is scanning, an increased immunity to interference is obtained or the requirements for the scanning unit can be made less restrictive.

Figure 2:
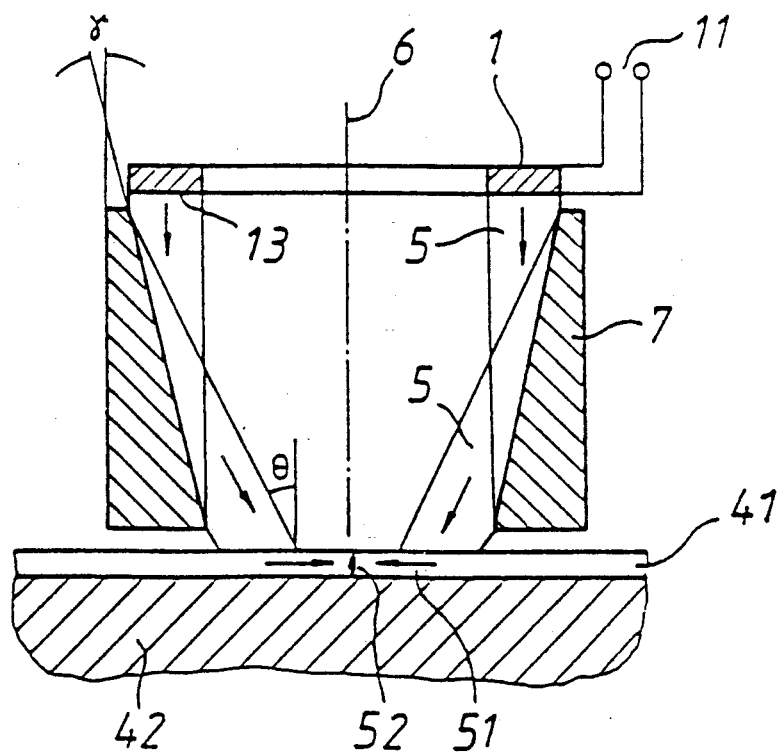
FIG. 2 shows a sectional view of a preferred embodiment with a conical reflector.

As an alternative embodiment, FIG. 2 shows an arrangement which includes a conical reflector 7, preferably made of metal, for example, polished aluminum. Identical parts are denoted by the same reference symbols as in FIG. 1. The ultrasonic transducer 1' is shaped to match the deflection element 7 as a circular ring which covers the projection of the reflector face onto its plane. The circular ring has a hole through its center. In this way, the ultrasonic power generated is fully utilized and the reception of specularly reflected ultrasonic waves 5 at the surface of the object 4 is avoided. The distance Z of the ultrasonic transducer 1' from the surface of the object 4 should preferably be selected with $Z < R / \tan\theta$, R being the outer radius of the reflecting face of the reflector 7, and $\theta$ being the angle of incidence of the ultrasonic waves on the object, which is linked by the law of reflection to the cone angle $\gamma$ of the reflector 7, as $\theta = 2\gamma$.

The inner radius r of the ultrasonic transducer 1', or of the reflecting face, should preferably be selected to be $r > R - Z \tan(\theta/2)$ so that the reflector does not sit on the object 4.

Figure 3:
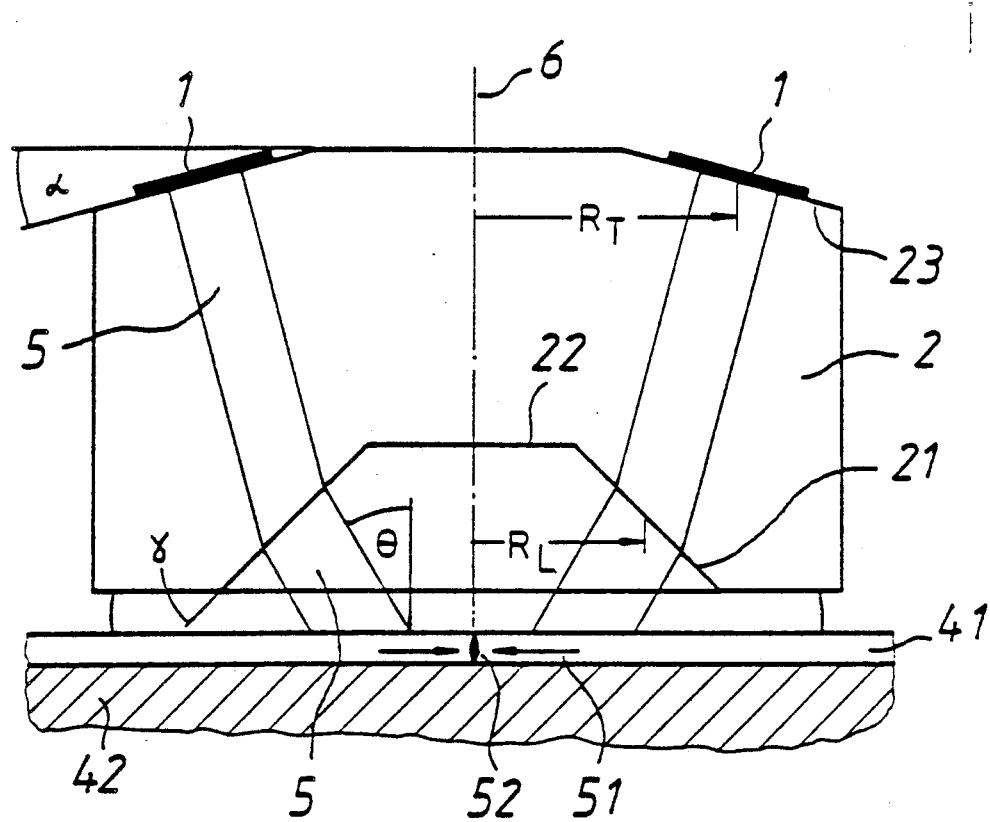
FIG. 3 shows a combination of a conical ultrasonic transducer and a conical lens.

FIG. 3 shows another embodiment which includes a conical ultrasonic transducer 1'', which otherwise corresponds to FIG. 1, with an ultrasonic lens 2''. Identical parts are denoted by the same reference symbols. In this embodiment, the lens body 2'' has a second cone face 23, on which a conical ultrasonic transducer 1'' is mounted. As a result, the ultrasonic radiation is cone-shaped and the energy density at the refracting face 21 is increased in comparison with the energy density at the ultrasonic transducer 1'', since the energy from the circular ring of the ultrasonic transducer 1'', with a mean radius $R_T$, is concentrated on the smaller circular ring of the diffracting face 21, with a mean radius $R_L$. Moreover, the projection of the refracting surface normal to the direction of the beam in 2 is increased, hence reducing diffraction losses.

This embodiment is particularly suitable for very small lens diameters, and can also be advantageously designed as a 180° sector.

While the invention has been described with reference to certain preferred embodiments, it is understood that various modifications and improvements may be made by those skilled in the art without departing from the scope of the present invention as defined by the appended claims.

What is claimed is:

1. A conical ultrasonic deflection system comprising:
    an ultrasonic transducer generating ultrasonic waves for ultrasonic microscopy using at least one of surface waves and Lamb waves in an object under examination; and
    an ultrasonic deflection element deflecting ultrasonic waves generated by said ultrasonic transducer to direct a conical wave front onto said object, said conical wave front defined by a deflection cone axis; and
    said ultrasonic transducer and ultrasonic deflection element preventing a portion of said object in the vicinity of said deflection cone axis from being influenced by undeflected waves; and
    wherein said ultrasonic transducer is cone shaped with a transducer cone axis of said ultrasonic transducer coinciding with said deflection cone axis.

2. A conical ultrasonic deflection system comprising:
    an ultrasonic transducer generating ultrasonic waves for ultrasonic microscopy using at least one of surface waves and Lamb waves in an object under examination; and
    an ultrasonic deflection element deflecting ultrasonic waves generated by said ultrasonic transducer to direct a conical wave front onto said object, said conical wave front defined by a deflection cone axis; and
    said ultrasonic transducer and ultrasonic deflection element preventing a portion of said object in the vicinity of said deflection cone axis from being influenced by undeflected waves; and
    wherein said ultrasonic deflection element includes a lens which has an inward conical face on an object side.

3. A conical ultrasonic deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein at least one of said ultrasonic transducer and said ultrasonic deflection element is approximately sector-shaped having a sector angle of 180°.

4. A conical ultrasonic deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein the frequency of said ultrasonic waves is selected such that the leaky Rayleigh or Lamb Wave signal is maximum.

5. A conical ultrasonic deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein said conical ultrasonic wave deflection system generates ultrasonic waves which excite Rayleigh or Lamb waves in a surface layer of said object.

6. A conical ultrasonic wave deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein a smallest diameter of said ultrasonic deflection element is more than several ultrasonic wavelengths.

7. A conical ultrasonic wave deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein said ultrasonic waves are generated in a range from 1 MHz to 10 GHz.

8. A conical ultrasonic wave deflection system comprising:

an ultrasonic transducer generating ultrasonic waves for ultrasonic microscopy using at least one of surface waves and Lamb waves in an object under examination; and an ultrasonic deflection element deflecting ultrasonic waves generated by said ultrasonic transducer to direct a conical wave front onto said object, said conical wave front defined by a deflection cone axis; and said ultrasonic transducer and ultrasonic deflection element preventing a portion of said object in the vicinity of said deflection cone axis from being influenced by undeflected waves; and wherein said conical ultrasonic wave deflection system operates as a transmitter and receiver simultaneously generating input signals for a reflecting ultrasonic microscope.

9. A conical ultrasonic wave deflection system as claimed in claim 2, wherein said conical face is in the shape of a truncated cone with a plane top face covered with a high ultrasonic wave damping layer.

10. A conical ultrasonic wave deflection system as claimed in claim 2, wherein said ultrasonic transducer is cone shaped with a transducer cone axis of said ultrasonic transducer coinciding with said deflection cone axis.

11. An ultrasonic conical wave front generating lens system, comprising:

an ultrasonic transducer generating ultrasonic waves for acoustic microscopy; and a solid lens element bonded to said ultrasonic transducer on one side of said solid lens element and having a conical refracting surface on another side of said solid lens element, said solid lens element deflecting ultrasonic waves generated by said ultrasonic transducer to direct a conical wave front onto an object, said conical wave front having an optimal vortex angle for exciting at least one of a leaky Rayleigh wave mode and a Lamb wave mode while avoiding excitation of compressional and shear waves in said object; and wherein said ultrasonic transducer and said solid lens element prevents a portion of said object in the vicinity of a cone axis of said conical refracting surface from being influenced by undeflected waves.

12. An ultrasonic conical wave front generating lens system as claimed in claim 11, wherein said ultrasonic transducer is plane shaped and said cone axis of said conical refracting surface is perpendicular to said ultrasonic transducer.

13. An ultrasonic conical wave front generating lens system as claimed in claim 11, wherein said ultrasonic transducer is cone shaped and wherein a transducer cone axis of said ultrasonic transducer coincides with said cone axis of said conical refracting surface.

14. An ultrasonic conical wave front generating lens system as claimed in claim 11, wherein said conical refracting surface is in the shape of a truncated cone recess in said solid lens element, with a plane top face of said recess being covered with a high ultrasonic wave damping layer.

15. An ultrasonic conical wave front generating lens system as claimed in claim 11, wherein at least one of said ultrasonic transducer and said solid lens element is approximately sector-shaped having a sector angle of 180°.

16. An ultrasonic conical wave front generating lens system as claimed in claim 11, wherein the frequency of said ultrasonic waves is selected such that one of a leaky Rayleigh wave signal and a Lamb wave signal is maximum.

17. An ultrasonic conical wave front generating lens system as claimed in claim 11, wherein said ultrasonic conical wave front generating lens system generates ultrasonic waves which excite at least one of Rayleigh waves and Lamb waves in a surface layer of said object.

18. An ultrasonic conical wave front generating lens system as claimed in claim 11, wherein a smallest diameter of said solid lens element is greater than several ultrasonic wavelengths.

19. An ultrasonic conical wave front generating lens system as claimed in claim 11, wherein said ultrasonic waves are generated in a range from 5 MHz to 10 GHz.

20. An ultrasonic conical wave front generating lens system as claimed in claim 1, wherein said ultrasonic conical wave front generating lens system operates as a transmitter and receiver simultaneously generating input signals for a reflection acoustic microscope.

21. An ultrasonic conical wave front generating lens system comprising:

a plane shaped ultrasonic transducer generating ultrasonic waves for acoustic microscopy; and a solid hollow truncated conical mirror element with a concave conical reflecting surface facing said ultrasonic transducer and with a cone axis of said mirror element perpendicular to said ultrasonic transducer to deflect ultrasonic waves generated by said ultrasonic transducer to direct a conical wave front onto an object, said conical wave front having an optimal vortex angle for exciting at least one of a leaky Rayleigh wave mode and a Lamb wave mode while avoiding excitation of compressional and shear waves in said object; and wherein said ultrasonic transducer and said solid hollow truncated conical mirror element prevents a portion of said object in the vicinity of a cone axis of said conical reflecting surface from being influenced by undeflected waves.

22. An ultrasonic conical wave front generating lens system as claimed in claim 21, wherein said ultrasonic transducer includes a hole axially aligned with said cone axis to prevent said portion of said object in the vicinity of said cone axis from being influenced by undeflected waves.

23. An ultrasonic conical wave front generating lens system as claimed in claim 21, wherein said ultrasonic transducer includes an inactive disk axially aligned with said cone axis to prevent said portion of said object in the vicinity of said cone axis from being influenced by undeflected waves.

24. An ultrasonic conical wave front generating lens system as claimed in claim 21, wherein at least one of said ultrasonic transducer and said solid hollow truncated conical mirror element is approximately sector-shaped having a sector angle of 180°.

25. An ultrasonic conical wave front generating lens system as claimed in claim 21, wherein the frequency of said ultrasonic waves is selected such that at least one of a leaky Rayleigh wave signal and a Lamb wave signal is maximum.

26. An ultrasonic conical wave front generating lens system as claimed in claim 21, wherein said ultrasonic conical wave front generating lens system generates ultrasonic waves which excite at least one of Rayleigh waves and Lamb waves in a surface layer of said object.

27. A conical wave front generating lens system as claimed in claim 21, wherein a smallest diameter of said solid hollow truncated conical mirror element is greater than several ultrasonic wavelengths.

28. An ultrasonic conical wave front generating lens system as claimed in claim 21, wherein said ultrasonic waves are generated in a range from 5 MHz to 10 GHz.

29. An ultrasonic conical wave front generating lens system as claimed in claim 21, wherein said ultrasonic conical wave front generating lens system operates as a transmitter and receiver simultaneously generating input signals for a reflection acoustic microscope.

* * * * *